United States Patent [19]

Kim

[11] Patent Number: 4,785,003
[45] Date of Patent: Nov. 15, 1988

[54] N-DISUBSTITUTED GLYCINE AND B-AMINO-PROPIONIC ACID DERIVATIVES HAVING ANTI-ULCER ACTIVITY

[75] Inventor: Sun H. Kim, Chestnut Hill, Mass.

[73] Assignee: Biomeasure, Inc., Hopkinton, Mass.

[21] Appl. No.: 821,071

[22] Filed: Jan. 21, 1986

Related U.S. Application Data

[62] Division of Ser. No. 661,354, Oct. 16, 1984, Pat. No. 4,598,067.

[51] Int. Cl.$^4$ .................... A61K 31/47; C07D 217/16
[52] U.S. Cl. ................................ 514/307; 530/317; 530/323; 544/349; 546/147
[58] Field of Search ..................... 546/147; 514/307

[56] References Cited

U.S. PATENT DOCUMENTS

| | | | |
|---|---|---|---|
| 4,234,588 | 9/1980 | Brown | 544/320 |
| 4,294,832 | 10/1981 | Yoneda et al. | 546/147 |
| 4,328,134 | 5/1982 | Schally | 260/112.51 R |
| 4,390,701 | 6/1983 | Algieri | 546/235 |
| 4,394,508 | 7/1983 | Crenshaw | 546/209 |
| 4,525,301 | 6/1985 | Henning et al. | 546/147 |

FOREIGN PATENT DOCUMENTS 0001174 8/1981 European Pat. Off. .
654065 7/1965 South Africa .

Primary Examiner—Glennon H. Hollrah
Assistant Examiner—James H. Turnipseed

[57] ABSTRACT

A compound having the formula

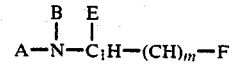

or a pharmaceutically acceptable salt thereof, wherein A is N-AC-Sar, pGlu, or homo-pGlu-; B is an aryl group, a heteroaryl group, a cycloalkyl group, an aralkyl group, a heteroalkyl group, a heteroaralkyl group, a benzoyl group, an alkyl group, an acetyl group, or a substituted aryl group wherein the substituent is halogen, hydroxy, alkoxy, nitro, cyano, or hydroxyalkyl; E is H or an alkyl group; B and E being separate substituents or, together with $C_1$ and the nitrogen atom to which B is attached, forming a 5,6, or 7-membered ring; m is an integer between 0 and 4; either F is

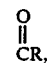

wherein R is an alkoxy group or an aralkoxy group; or F is

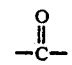

and is capable of forming a 6-membered ring with the nitrogen atom of A, provided that F can only be

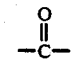

forming a ring with A when A is pGlu or homo-pGlu.

6 Claims, No Drawings

N-DISUBSTITUTED GLYCINE AND B-AMINO-PROPIONIC ACID DERIVATIVES HAVING ANTI-ULCER ACTIVITY

This application is a divisional of Kim, U.S. Ser. No. 661,354, filed Oct. 16, 1984, issued July 1, 1986 as U.S. Pat. No. 4,598,067.

BACKGROUND OF THE INVENTION

This invention relates to antiulcer compounds.

SUMMARY OF THE INVENTION

In general, the invention features compounds having the formula

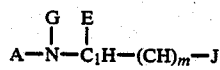

(1)

or a pharmaceutically acceptable salt thereof, where A is N-acetyl-sarcosine (N-Ac-Sar) $HOOCCH_2N(CH_3)CH_2COOH$, pyroglutamate (pGlu)

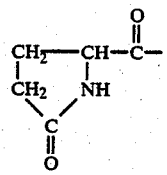

or homo-pyroglutamate (homo-pGlu)

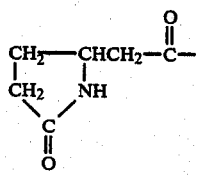

G is an aryl group having between 6 and 12, inclusive, carbon atoms (e.g., phenyl), a heteroaryl group having between 3 and 12, inclusive, carbon atoms (e.g., imidazolyl), a substituted aryl group where the substituent is halogen, hydroxy, alkoxy having 1 to 3, inclusive, carbon atoms, nitro, cyano, or hydroxyalkyl having 1 to 3, inclusive, carbon atoms, a cycloalkyl group having between 3 and 7, inclusive, carbon atoms (e.g., cyclohexyl), an aralkyl group having between 7 and 17, inclusive, carbon atoms (e.g., benzyl), a heteroalkyl group having between 1 and 5, inclusive, carbon atoms (e.g., thioalkyl), a heteroaralkyl group (e.g., 4-imidazole ethyl), a benzoyl group, an alkyl group having between 1 and 5, inclusive, carbon atoms (e.g., methyl or ethyl), or an acetyl group; E is H or an alkyl group having between 1 and 5, inclusive, carbon atoms; G and E either being separate substituents or, together with $C_1$ and the nitrogen atom to which G is attached, forming a 5, 6, or 7-membered ring; m is an integer between 0 and 4, inclusive; and either J is

CR, where R is a hydroxy group, an aralkoxy group having between 7 and 17, inclusive, carbon atoms (e.g., benzyloxy), or an alkoxy group having between 1 and 3, inclusive, carbon atoms; or J is

and can form a 6-membered ring with the nitrogen atom of A, provided that J can only be

forming a ring with A when A is pGlu or homo-pGlu. (When no isomer designation is given with reference to an amino acid, the L-isomer is intended.)

In other preferred embodiment, B is phenyl, benzyl, or benzoyl; E is H, methyl, or ethyl; and G and E, together with $C_1$ and the nitrogen atom to which G is attached, form a 5, 6, or 7-membered ring having the formula

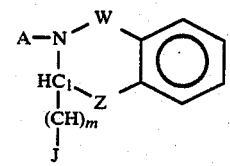

where W is nothing, $-CH_2-$, or

and Z is nothing, $-CH_2-$, or $-CH_2CH_2-$.

In other preferred embodiments, G is ethyl, thiomethyl, acetyl, or E is methyl, ethyl, or propyl; and G and E, together with $C_1$ and the nitrogen atom to which G is attached, form a 5, 6, or 7-membered ring having the formula

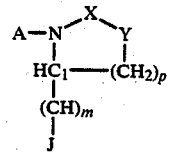

where X and Y, together, are $-CH_2CH_2-$, $-CH_2S-$,

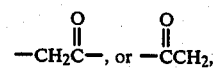

and p is an integer from 1 to 3, inclusive.

Preferred compounds of the invention include N-(pyroglutamyl)-N-benzylglycine; N-(pyroglutamyl)-N-benzylglycine ethylester; N-(N'-acetylsarcosyl)-N-benzylglycine; N-(N'-acetylsarcosyl)-N-benzylglycine ethylester; β-[N-(pyroglutamyl)-N-benzyl]aminopropionic acid; ethyl-β-[N-(pyroglutamyl)-N-benzyl]aminopropionate; β-[N-(N'-acetylsarcosyl)-N-benzyl]aminopropionic acid; ethyl-β-[N-(N'-acetylsarcosyl)-N-benzyl]aminopropionate; 1-benzylpyrrolo(1,5-c)-piperazine-3,6,9-trione; N-(N'-acetylsarcosyl)-1,2,3,4-tetrahydroisoquinoline-3-carboxylic ethyl ester; and N-(N'-acetylsarcosyl)-1,2,3,4-tetrahydroisoquinoline-3-carboxylic acid; or pharmaceutically acceptable salts thereof.

In other preferred embodiments, a therapeutically effective amount of the therapeutic compound and a pharmaceutically acceptable carrier substance, e.g., magnesium carbonate or lactose, form a therapeutic composition, e.g., a pill, tablet, capsule, or liquid for oral administration to a patient; a liquid capable of being administered nasally to a patient; or a liquid capable of being administered intravenously, parenterally, subcutaneously, or intraperitoneally.

The compounds of the invention are effective in treating gastric, peptic, or duodenal ulcers. They are stable, inexpensive, non-toxic, and non-mutagenic.

Other features and advantages of the invention will be apparent from the following description of the preferred embodiments thereof, and from the claims.

DESCRIPTION OF THE PREFERRED EMBODIMENTS

We now describe the structure, synthesis, and use of preferred embodiments of the invention.

Structure

The compounds of the invention have the general formula recited in the Summary of the Invention above. Examples of preferred compounds within this formula are those referred to as preferred embodiments above.

The compounds of the invention are N-disubstituted glycine or N-disubstituted B-aminopropionic acid derivatives; the tertiary amines thus created confer stability to the compounds. The N-substituents include an L- or D- amino acid (pGlu, homo-pGlu, or N-AcSar) and an aryl, heteroaryl, benzoyl, aralkyl, heteroalkyl, cycloalkyl, alkyl, heteroaralkyl, or acetyl group; these groups can be substituted or unsubstituted.

When the compound is an N-disubstituted glycine in which one of the substituents is pGlu or homo-pGlu, a 6 membered ring can form between the nitrogen atom of the pGlu or homo-pGlu group and the carbonyl of the glycine group. Cyclization reactions to form 4, 5, 6, or 7 membered rings between the nitrogen and $C_1$ atoms of the glycine or B-amino propionic acid groups is also possible.

The compounds can also be provided in the form of pharmaceutically acceptable salts. Examples of suitable salts include those formed with hydrochloric, hydrobromic, sulfuric, maleic, or fumaric acid; potassium, sodium, or aluminum hydroxide; or dicyclohexylamine.

Synthesis

The above compounds can be synthesized as follows. First, a compound of formula (2), (3), or (4):

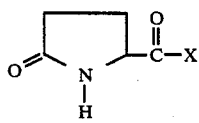 (2)

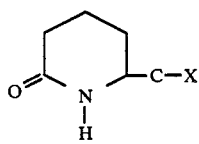 (3)

-continued

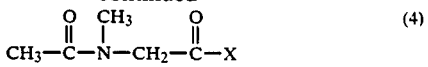 (4)

where X represents a hydroxyl or carboxyl acid activating group, e.g., a halogen such as chlorine, is condensed with a secondary amino-ester of formula (5)

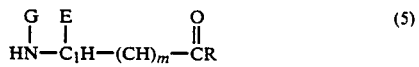 (5)

where R is lower (between one and three, inclusive, carbon atoms) alkoxy or aralkoxy and m is between 0 and 4, inclusive.

The corresponding acids are then prepared from these compounds by hydrolyzing the esters with aqueous base. When compounds (2) or (3) are condensed with compound (5) in which m=0, intramolecular cyclization via nucleophilic displacement of R by the nitrogen of compounds (2) or (3) can take place, resulting in the formation of a 6-membered ring.

Compounds within formulae (2), (3), (4), and (5) are commercially available; alternatively they can be synthesized according to standard methods, e.g., as described in Greenstein et al. *Chemistry of the Amino Acids*, Vols. 1-3, J. Wiley, New York (1961); and *J. Pharm. Sci.*, 51, 1058 (1962).

The condensation reactions are preferably carried out in an inert polar organic solvent, e.g., dimethylformamide, tetrahydrofuran, acetonitrile, or dichloromethane, using a suitable mild condensing agent, e.g., dicyclohexylcarbodiimide (DCC), and, optionally, a catalyst, e.g., 1-hydroxybenzotriazole. The reaction temperature is maintained below room temperature (−15° C. to room temperature) in order to minimize side reactions. Typical suitable condensation procedures are described in Schroeder et al., The Peptides, Vols. 1-2 (1965, 1966) and Gross et al., The Peptides, Vols. 1-3 (1979, 1980, 1981).

The intermediate and final products are isolated and purified by standard methods, e.g., column chromatography or crystallization. Purity is determined using chromatographic, spectroscopic, and chemical analysis.

Specific compounds are made as follows.

N-(pyroglutamyl)-N-benzylglycine ethylester

A cold solution of 2.48 g DCC in 10 ml dimethylformamide is added to a stirred ice-cooled solution of 1.5 g pyroglutamic acid, 2.18 g N-benzylglycine ethylester, and 3.13 g 1-hydroxybenzotriazole in 20 ml dry dimethylformamide, and the resulting solution is stirred at 0° C. for 1 hr and then at room temperature overnight. It is then filtered and the solvent evaporated in vacuo to dryness. The residue is dissolved in 150 ml chloroform, washed with 5% aq $NaHCO_3$ and water, and dried over anhydrous $MgSO_4$. Following evaporation of solvent, the residue is chromatographed on silica gel (55 g) using chloroform followed by chloroform/methanol (20:1). Appropriate fractions are pooled and the solvent removed in vacuo to yield 2.6 g of the product as an oil. TLC: (silica gel; $CHCl_3/MeOH=9:1$) $R_f=0.45$.

N-(pyroglutamyl)-N-benzylglycine and 1-benzylpyrrolo[1,5-c]-piperazine-3,6,9-trione 1.25 g N-(pyroglutamyl)-N-benzylglycine ethylester is dissolved in 5 ml methanol, treated with 3 ml 2N NaOH, and stirred for 5 min., after which the solution is concentrated to a small volume by removal of solvents. The residue is then dissolved in 10 ml H₂O, acidified to pH2, extracted several times with ethyl acetate, and dried over anhydrous MgSO₄. Following evaporation of solvent, the residue is chromatographed on silica gel (55 g) using chloroform/methanol/acetic acid (4:1:0.1). The first fractions give 0.36 g N-(pyroglutamyl)-N-benzylglycine as a white solid. TLC: (silica gel; CHCl₃/MeOH/HOAC=4:1:0.1) $R_f$=0.6, Mass: 276 (molecular ion).

Later fractions afford 0.18 g 1-benzylpyrrolo[1,5-c]-piperazine-3,6,9-trione, the result of intramolecular cyclization, as a foamy solid. TLC: (silica gel; CHCl₃/MeOH/HOAC=4:1:0.1) $R_f$=0.2, Mass: 258 (molecular ion).

Ethyl-β-[N-(pyroglutamyl)-N-benzyl]aminopropionate and β-[N-(pyroglutamyl)-N-benzyl]aminopropionic acid are prepared in analogous fashion by substituting ethyl-β-[N-benzyl]-aminopropionate for N-benzylglycine ethylester.

N-(N'-acetylsarcosyl)-N-benzylglycine ethylester

A cold solution of 1.65 g DCC in 3 ml dimethylformamide is added to a stirred ice-cooled solution of 1.0 g N-acetylsarcosine and 1.4 g N-benzylglycine ethylester in 9 ml dry dimethylformamide, and the resulting solution is stirred at 0° C. for 1 hour and then at room temperature for 2 hours. It is then filtered and the precipitate is washed with dimethylformamide. The filtrate and washings are combined and the solvent is evaporated to dryness in vacuo to yield a residue which is then dissolved in 30 ml chloroform, washed with 5% aq. NaHCO₃ and water, and dried over anhydrous MgSO₄. Evaporation of solvent produces the desired ester which is either isolated (m.p. 98°-101° C.) or hydrolyzed directly to form the corresponding acid, N-(N'-acetylsarcosyl)-N-benzylglycine.

N-(N'-acetylsarcosyl)-N-benzylglycine

Crude N-(N'-acetylsarcosyl)-N-benzylglycine ethylester from the above preparation is dissolved in 8 ml ethanol, treated with 10.8 ml 1N NaOH, and stirred for 10 min, after which the solution is diluted with 30 ml water and extracted several times with ether. The aqueous layer is then adjusted to pH1, extracted several times with ethyl acetate, and dried over anhydrous MgSO₄. Following evaporation of solvent, the residue is recrystallized from methanol-ether to yield 1.16 g of the desired acid (m.p. 135°-136° C.). TLC: (silica gel; CHCl₃/MeOH/HOAC=6:2:0.5) $R_f$=0.58. Anal. calc'd. for C₁₄H₁₈N₂O₄: C, 60.41; H, 6.51; N, 10.06 Found: C, 60.16; H, 6.43; N, 10.08

Ethyl-β-[N-(N'-acetylsarcosyl)-N-benzyl]aminopropionte and β-[N-(N'-acetylsarcosyl)-N-benzyl]aminopropionic acid are prepared in analogous fashion by substituting ethyl-β-[N-benzyl]aminopropionate for N-benzylglycine ethylester.

Benzyl-β-[N-(pyroglutamyl)-N-(4-ethylimidazolyl)-]aminopropionate and Benzyl-β-[N-(N'-acetylsarcosyl)-N-(4-ethylimidazolyl)]aminopropionate These compounds can be prepared by condensing benzyl-β-[N-(4-ethylimidazolyl)]aminopropionate, formed from the reaction of histamine with benzylacrylate, with either pyroglutamic acid or N-acetylsarcosine according to the above-described methods; the corresponding acids can be prepared via catalytic hydrogenation of the product esters using Lindlar's catalyst.

N-(N'-acetylsarcosyl)-1,2,3,4-tetrahydroisoquinoline-3-carboxylic ethyl ester This compound can be prepared by condensing 1,2,3,4-tetrahydroisoquinoline-3-carboxylic ethyl ester with N-acetylsarcosine according to the above-described methods; the corresponding acid can be prepared via catalytic hydrogenation of the product ester using Lindlar's catalyst or via base hydrolysis.

Use

When administered to a patient (e.g., orally, intravenously, parenterally, nasally, or by suppository), the compounds are effective in the treatment of gastric, peptic, and duodenal ulcers, especially those induced by dimaprit, indomethacin, and aspirin.

The compounds can be administered to a human patient in a dosage of 5-500 mg/kg/day, preferably 25 mg/kg/day.

Other embodiments are within the following claims.

I claim:

1. A compound having the formula

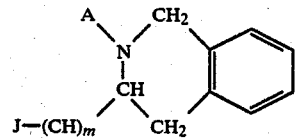

or a pharmaceutically acceptable salt thereof, wherein
A is N-Ac-Sar, pGlu, or homo-pGlu;
m is either an integer between 1 and 4, inclusive, when A is N-Ac-Sar, or an integer between 0 and 4, inclusive, when A is pGlu or homo-pGlu; and
J is

wherein R is a hydroxy group, an alkoxy group having between 1 and 3 carbon atoms, inclusive, or an aralkoxy group having between 7 and 17 carbon atoms, inclusive.

2. The compound of claim 1 having the name N-(N¹-acetylsarcosyl)-1,2,3,4-tetrahydroisoquinoline-3-carboxylic ethyl ester; or a pharmaceutically acceptable salt thereof.

3. The compound of claim 1 having the name N-(N¹-acetylsarcosyl)-1,2,3,4-tetrahydroisoquinoline-3-carboxylic acid; or a pharmaceutically acceptable salt thereof.

4. An antiulcer composition comprising a therapeutically effective amount of the compound of claim 1 together with a pharmaceutically acceptable carrier substance.

5. A method of treating an ulcer in a mammal comprising administering to said mammal a therapeutically effective amount of the compound of claim 1.

6. The therapeutic composition of claim 4 wherein said composition is in the form of a pill tablet, capsule, or liquid for oral administration to a patient in need of said compound.

* * * * *